United States Patent [19]

Tutt et al.

[11] 4,100,401

[45] Jul. 11, 1978

[54] CALORIE CALCULATOR-CHRONOMETER

[76] Inventors: Eugene F. Tutt; Rita C. Tutt, both of 1501 Nisson Rd., Tustin, Calif. 92680

[21] Appl. No.: 758,917

[22] Filed: Jan. 13, 1977

[51] Int. Cl.² .............................................. G06M 3/08
[52] U.S. Cl. .............................. 235/92 T; 235/92 EV; 235/92 CP; 235/92 R; 58/152 R; 364/413; 364/705
[58] Field of Search .......... 235/92 EV, 92 T, 92 MT, 235/92 CP, 156; 58/152 R, 23 R; 128/2.06 F, 2.05 T

[56] References Cited

U.S. PATENT DOCUMENTS

| | | | |
|---|---|---|---|
| 3,777,475 | 12/1973 | Grossan | 58/152 R |
| 3,803,834 | 4/1974 | Reese | 58/152 R |
| 3,928,960 | 12/1975 | Reese | 58/152 R |
| 3,955,355 | 5/1976 | Luce | 235/156 |
| 4,019,037 | 4/1977 | Takashi Monna | 235/156 |
| 4,022,014 | 5/1977 | Lowdenslager | 235/156 |
| 4,024,678 | 5/1977 | Portmann et al. | 58/23 R |

*Primary Examiner*—Joseph M. Thesz
*Attorney, Agent, or Firm*—Weiss & Ptak

[57] ABSTRACT

A solid-state electronic wristwatch with a digital display includes additional circuitry to permit utilization of the display and the source of constant frequency signals of the watch to expand its operation to a calorie calculator. The calorie calculator components include a counter circuit for entering a count indicative of caloric intake, circuitry for entering calorie expenditure rate in terms of calories expended per hour, and a main calorie counter into which the calorie input information is entered and from which counts representative of calories consumed are removed at a rate determined by the calorie expenditure rate entered into the system. The watch display may be activated to display the calories being added, the calorie expenditure rate, and the net calories unconsumed on demand by the user. The watch also, if desired, may include a calendar display which also shares the common digital display elements used to display the time and calorie information.

4 Claims, 4 Drawing Figures

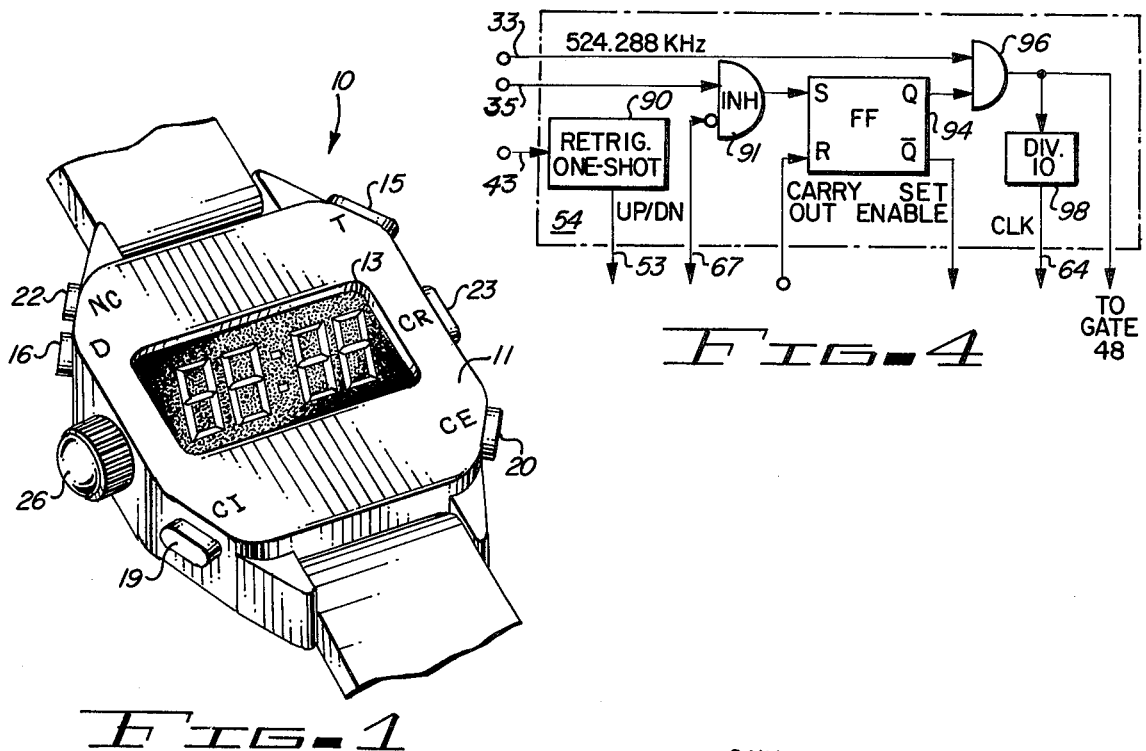
FIG-1
FIG-4
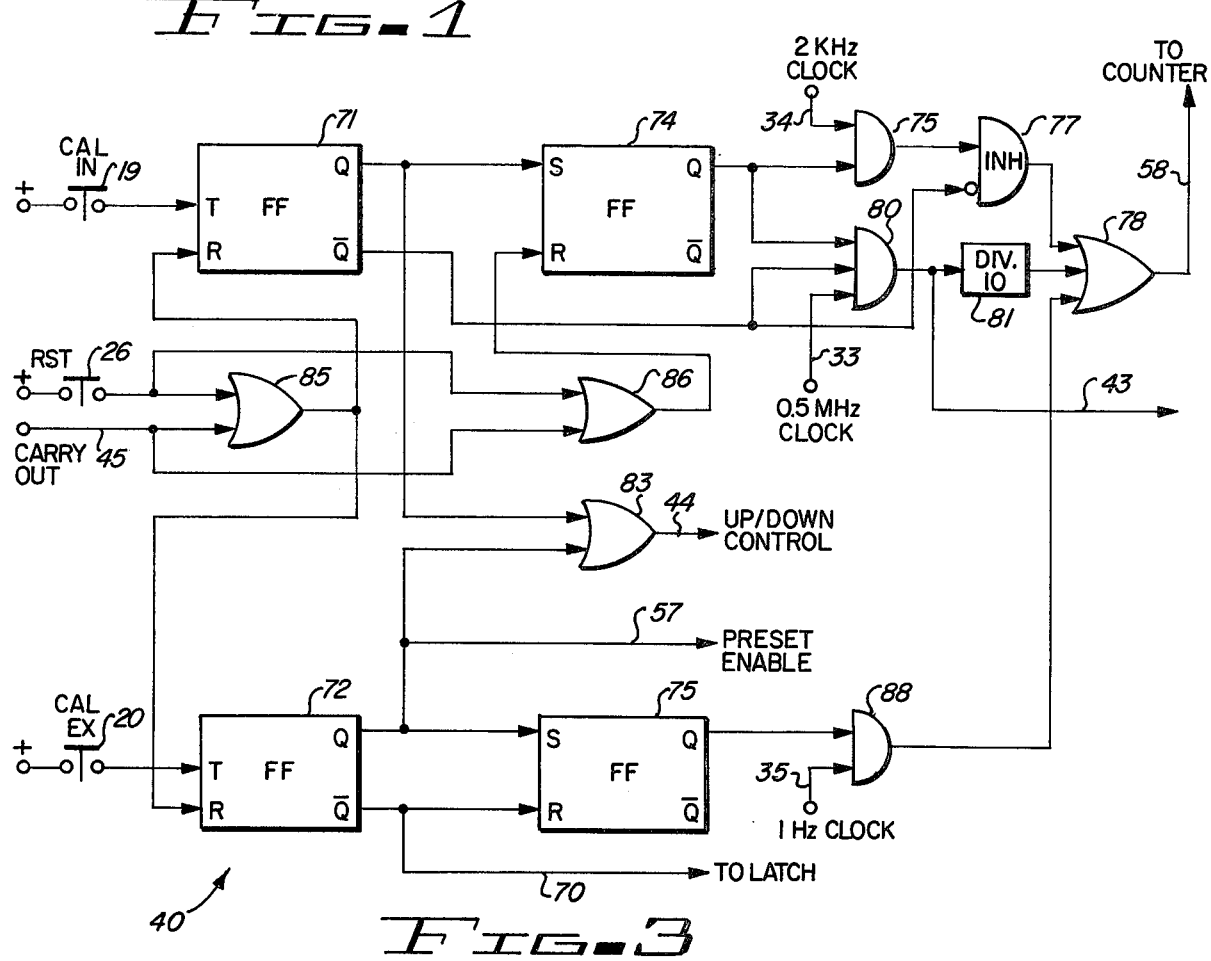
FIG-3

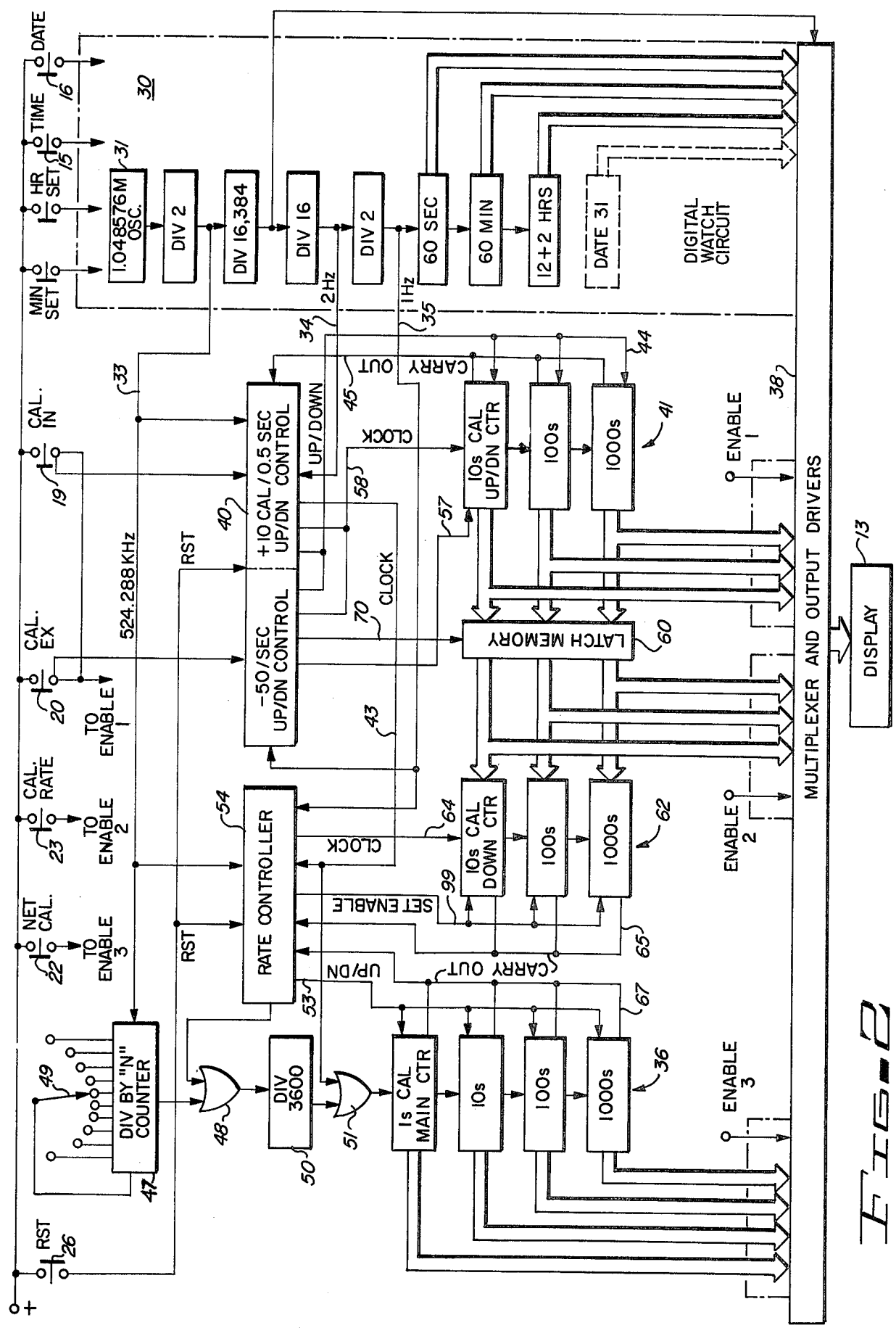

CALORIE CALCULATOR-CHRONOMETER

BACKGROUND OF THE INVENTION

A large percentage of the adult United States population is overweight or is prone to be overweight. Bookstores carry entire sections devoted to books which their readers hope will provide an easy solution to their weight problems. Dietetic foods, drugs, weight reducing programs, machines and treatments abound, and millions of dollars are spent in an effort by overweight persons to solve their weight problems.

Competent medical specialists who have studied the problems of obesity generally are convinced, however, that the only effective method of controlling weight is to balance the intake of energy in the form of food with the expenditure of energy in the form of activity. Whenever an imbalance exists in the form of a greater energy intake than is expended, an increase in weight results. In theory, the maintenance of a balanced caloric intake/expenditure should be easily established. Readily available charts have been published which provide accurate data on the caloric content of all types of foods and beverages. In addition, caloric expenditures of a wide range of human activities from sleep through strenuous exercise have been measured and charted. Many thousands of individuals have succeeded in achieving their desired weight and maintaining that weight by balancing their caloric intake with expenditure. Many persons carry calorie counter charts with them wherever they go to limit their caloric intake in a given day to some maximum amount which they or their doctors have determined should not be exceeded if a weight loss is to be attained or maintenance of a given weight is to be established.

Some persons appear to have a built-in ability to strike the right balance between caloric intake and expenditure. For a large number of persons however, perhaps the vast majority, it is necessary to keep a record of the calories consumed and the activities performed and the duration of such performance in order to maintain an effective caloric balance. To be truly effective, data of this type must be accurate and must be continuously accounted for 24 hours of every day.

Anyone who has observed a person on a diet is well aware of the inconvenience of the collection and recording of such data and performing the addition, subtraction and multiplication required to produce meaningful information relative to caloric intake, expenditure, and remaining unexpended calories. This inconvenience most likely is responsible for the fact that only a relatively small number of persons use this technique, even though it is an effective solution to the widespread problem of calorie control.

Solid-state battery-powered electronic wristwatches utilizing digital displays in the form of light-emitting diodes or liquid crystals are enjoying increasing popularity. A typical watch of this type is disclosed in U.S. Pat. No. 3,803,827 to Dennis A. Roberts, issued Apr. 16, 1974. The electronic wristwatch of that patent is provided with a master time reference in the form of a high frequency oscillator connected to the watch display through suitable divider circuits to provide indicia of the time on demand by operation of a switch to energize a plurality of light-emitting diodes. The time computer portion of the watch circuit continuously keeps the time although it is only displayed upon demand. The display and the driver circuits for the display also are shared by a calendar calculating circuit which may be coupled to the display diodes upon demand by operation of a calendar display switch.

Digital electronic wristwatches have been combined in a single housing with a miniature calculator in which the calculator output display also shares the display elements which are used to display the time or calendar information. Thus, techniques presently are available in improved electronic watch constructions which permit sharing of the time display elements for other purposes.

It is desirable to incorporate a calorie counter into an electronic wristwatch which will enable the user to readily enter caloric intake information into the wristwatch/calorie calculator, determine a caloric rate expenditure, and have readily available on a continuous basis data indicative of the excess of calorie intake over calorie expenditures. This then would provide the user, at any time, the data necessary to see the state of his calorie intake/expenditure account; so that he can modify his future calorie intake or his activity or both to achieve the results he wants with his own diet program.

SUMMARY OF THE INVENTION

It is an object of this invention to provide an improved calorie counting system.

It is another object of this invention to provide an improved electronic timepiece with additional data handling capabilities.

It is an additional object of this invention to provide an improved calorie calculator-chronometer system.

It is a further object of this invention to provide an electronic wristwatch having a digital display with additional circuitry to permit the use of the watch as a calorie calculator.

An electronic timepiece, which includes a source of constant frequency signal pulses, a time computing circuit coupled to the source of pulses where the time computing circuit produces time information in binary coded form to a decoder which couples the time computing circuit to an electro-optical digital display, also includes an auxiliary data system. The auxiliary data system has a storage counter in it for storing numerical data indicative of preestablished information. A manually operated switch is coupled with the storage counter and is used to effect the storage of data in it. A circuit couples the counter with the source of constant frequency signal pulses to change the numerical data stored in the counter at a preestablished rate, and a circuit including an additional manually operated switch is used to couple the counter with a decoder circuit for energizing the digital display from the counter in response to operation of the additional switch.

BRIEF DESCRIPTION OF THE DRAWING

FIG. 1 is a perspective view of a wristwatch incorporating a preferred embodiment of the invention;

FIG. 2 is a block diagram of a circuit implementing a preferred embodiment of the invention; and FIGS. 3 and 4 are more detailed block diagrams of a portion of the circuit shown in FIG. 2.

DETAILED DESCRIPTION

In the drawings, the same reference numbers are used throughout the several figures to designate the same or similar components. Referring to FIG. 1, there is shown a perspective view of a wristwatch generally indicated at 10. The watch comprises a case 11 having a viewing window 13 in it for viewing a typical digital display, comprising four seven-segment display elements, the middle two of which are separated by a colon or other symbol. These display elements may be light-emitting diodes, liquid crystal elements or some other suitable conventional display devices.

Typically, in an electronic wristwatch of this type, particularly when the display elements are in the form of light-emitting diodes, the display is not energized during normal operation of the watch. The time computer circuit of the watch, however, continuously computes the current time; and upon depression of a time pushbutton 15, the display is energized to indicate the current time in hours and minutes. In addition, the continued depression of a time pushbutton 15 may be used to effect a display of seconds information, if desired. Many watches of this type include an additional display energizing pushbutton 16 which is used to activate a calendar computing circuit within the watch and connect it to the display. When the button 16 is depressed, the display is illuminated with the current month and date information. Since the display in the window 13 is only activated when specific information is demanded, it may be shared with both the time computing circuit and the calendar circuit since only one or the other of these is activated at any one time to provide the desired information. The manner in which such a display is shared is conventional and well known and simply utilizes a multiplexing gate decoder arrangement to drive the display from the selected one of the data input circuits, that is, either the time computing circuit or the calendar circuit.

The watch shown in FIG. 1 has been further modified to operate as a calorie calculator system; and for this purpose it includes additional pushbuttons. A pushbutton 19 is activated to enter calorie intake information in response to internal timing circuitry within the wristwatch case 11. As this information is being entered, the display in the window 13 shows the accumulating count of the calorie intake entry. In the system described more fully in conjunction with FIGS. 2 and 3, a second depression of the pushbutton 19 terminates the entry of further calorie input data and sets up a transfer of the input data to a main calorie counter which continuously provides a count of the accumulated calories which have not been expended by the user. Since calories are expended by a person at different rates depending upon his physical activity, a calorie rate expenditure pushbutton 20 is used to enter calorie rate expenditure data into another portion of the calorie calculator circuitry. This again is done in conjunction with the timing circuitry already available within the wristwatch for running the time computer circuitry; and the display in the window 13 indicates the accumulation of the calorie expenditure per hour entry as it is made. A second depression of the pushbutton 20 transfers this information to another portion of the calorie computer circuitry where it is utilized to control the operation of the main calorie counter.

Any time the user of the calorie computer wristwatch shown in FIG. 1 desires to know his net calorie count, representative of the excess of calorie intake over calories expended which he has for the time interval under consideration, he depresses a pushbutton 22 which couples the output of a net main calorie counter to the display to give the desired reading. In addition, if at any time the user is uncertain as to the calorie expenditure rate which he has set into the calorie computer portion of his wristwatch, a pushbutton 23 is depressed to provide a reading of the current calorie expenditure rate stored within the calorie computer section of the watch.

Finally, in order to reset the operation of the system for the entry of new data, a reset pushbutton 26 is provided. The various pushbuttons for controlling the display in the window 13 conveniently may be located about the periphery of the watch case as illustrated in FIG. 1. The particular location of the pushbuttons is not important, however; and if desired, some of them or all of them could be located directly on the watch case face. In addition to the control pushbuttons which have been shown in FIG. 1, there generally are pushbuttons or controls to enable setting of the current time and data in the watch initially and whenever a battery replacement is made or if the watch should fail to keep correct time for any reason.

Reference now should be made to the circuit of FIG. 2 which illustrates the addition of the calorie computer to a conventional electronic digital watch circuit. The watch function is similar to existing units, such as the type disclosed in U.S. Pat. No. 3,803,827, to which reference previously has been made. The conventional watch circuit 30 is shown within the dashed lines on the righthand side of the drawing of FIG. 2. The circuit 30 typically includes a stable high-frequency oscillator 31 which operates as the source of constant frequency signal pulses used in the time computing circuitry 30 of the watch, the calendar computing circuitry, and in the calorie computer circuitry forming the remainder of the circuit of FIG. 2.

As shown in FIG. 2, the conventional time computer watch circuitry divides down the output frequency of the oscillator 31 to produce output pulses at different frequencies. Three of these frequencies are utilized in the calorie computer portion of the circuit shown in FIG. 2. The highest frequency is one-half the basic oscillator frequency and appears on a lead 33. As illustrated, this frequency is slightly more than one-half megahertz, namely 524.288 kilohertz. Two other frequencies are supplied from the frequency divider chain in the watch circuit 30 and these are a 2 Hertz frequency supplied on a lead 34 and 1 Hertz frequency supplied on a lead 35. Pulses at these three different frequencies are continuously supplied on the leads 33 through 35.

In the calorie computer portion of the circuit, three digital counters function as the primary control elements of the circuit. The first of these counters is a reversible main calorie counter 36 which is the counter in which the net calorie information is continuously stored and updated. At any time the net calorie pushbutton 22 is depressed, it enables coincidence gate circuitry in a conventional multiplexer gate and output driver circuit 38 to display on the digital display in the window 13 the calorie count then present in the counter circuit 36. This display exists as long as the button 22 continues to be depressed.

The multiplexer and output driver circuit 38 is a conventional one and merely is a straightforward expansion of the comparable circuit which is used to share the same display and output drivers of a conventional wristwatch between the time computer section of the watch and the calendar computer section of the watch. Typically, this circuitry includes coincidence gates which are enabled by depression of the selected pushbutton to connect the driver and decoder circuitry for the display with the appropriate inputs supplied by the selected circuit.

The main calorie counter 36 is designed to provide a running algebraic total of calories which have been added to and subtracted from the system for display at any given time. Calories are added to the system by depressing the Calorie In pushbutton 19, as stated previously, releasing the button when the desired number of calories have been entered, and then depressing the button 19 a second time to enter the data into the main calorie memory 36.

The Calorie in pushbutton 19 operates an up/down control circuit 40 which in turn controls the entry of clock pulses into an auxiliary binary counter 41 at a 2 Hertz rate to increment the counter 41 by a count of +10 calories each one-half second. So long as the pushbutton 19 is depressed, the "Enable 1" input to the multiplexer gate and output driver circuit 38 is enabled; so that the outputs of the counter 41 are used to drive the display 13. Once the desired calorie count for the input is indicated in the display 13, the pushbutton 19 is released. The pushbutton 19 then is depressed a second time to cause the total count in the auxiliary counter 41 to be transferred under control of high speed clock signals applied over a lead 43 to increment the main counter 36 by the amount of the count stored in the counter 41. This same source of clock pulses is used to drive the counter 41 in its reverse direction; and when it is emptied, a carryout pulse is applied over a lead 45 to the control circuit 40 to terminate the transfer operation. At this point, a count corresponding to the additional calories has been added to the count in the counter 36; and the counter 41 is cleared.

The basic circuitry of FIG. 2 is designed to decrease the count in the main calorie counter 36 approximately one calorie per minute. This represents the basal fraction expended in sustaining body functions at rest. However, not all persons have this same basal fraction; so an adjustment may be effected by a divide-by-"N" counter 47, the division ratio of which is varied by the setting of an adjustable switch 49. This type of counter is well known in the art, and the manner of changing or adjusting its division number or ratio may be readily effected. In the circuit of FIG. 2, the adjustment is made to adjust the basal fraction rate applied to the input of the first stage of the counter 36 from approximately −0.5 calories per minute to −1.5 calories per minute. This permits the calorie calculator operation to be tuned or adjusted to the particular metabolic rate of the user. This adjustment and the minute and hour setting controls for the watch preferably are located on the back of the case of the watch since these controls are infrequently used.

As illustrated, the pulses which are used to decrement the counter 36 are obtained from the lead 33 and are applied through the variable divide-by-"N" counter 47 to one input of an OR gate 48. The pulses then are passed through a divide-by-3600 circuit 50 which applies the resultant pulses through an OR gate 51 to the input stage of the counter 36. The particular frequencies which have been shown and the divider circuits are selected so that pulses applied from the output of the OR gate 51 to the counter 36 occur at the basal fraction rate of approximately one pulse per minute (±0.5 pulses per minute).

Normally the counter 36 is operated in its count down mode of operation, that is each pulse applied to the input of the first stage causes a decrease in the binary count of the counter by one unit. The direction of count of the counter 36, which can count in either direction, however, is controlled by the signal on a lead 53 from a rate controller circuit 54. At the time the transfer clock pulses are applied over the lead 43 through the OR gate 51 to increase the count in the counter 36, the same clock pulses are applied to the rate controller 54 to cause it to apply an "up" count signal on the lead 53 to the counter 36. Thus, whenever pulses are being transferred over the lead 43, indicative of the transfer of calorie input information from the counter 41 to the counter 36, the rate controller 54 provides an output on the lead 53 to cause the counter 36 to count in its "up" direction. At all other times, the counter 36 counts in its down direction in response to the pulses applied to it from the output of the OR gate 51.

In addition to the basal calorie expenditure which is set or controlled by the variable counter 47, activity in addition to the basal rate results in increased expenditure or consumption of calories. The calorie expenditure rate varies in accordance with the activity, as is readily apparent. Charts are available which provide fairly accurate representations of the rates of expenditure or burning of calories for different activities. When the user of the calorie calculator-chronometer circuit shown in FIG. 2 changes his activity from any previous activity to a new one, it is necessary to adjust the basal calorie expenditure provided by the output of the counter 47 by the new activity. This is accomplished by depressing the calorie expenditure pushbutton 20. As stated previously, this causes the Enable 1 display output to drive the display 13 from the output of the auxiliary counter 41. At the same time, the up-down control signal from the control circuit 40 applied over the lead 44 cuases the counter 41 to be placed in its "up" mode of operation.

A "jam" input to the counter 41 is applied over a lead 57 to the counter to cause it to increase its count by 50 each time a clock pulse is applied to the counter over the lead 58. The circuit is set up to apply clock pulses at one second intervals over the lead 58 when the button 20 is depressed, so that the display in the display window 13 changes by a count of 50 each time a pulse appears on the lead 58. When the desired calorie expenditure rate is displayed in the window 13, the pushbutton 20 is released. The button 20 then is depressed a second time, and this causes the circuit 40 to shift the count now representative of the calorie expenditure rate in the counter 41 to a latch memory circuit 60. Here the count is stored indefinitely until a new calorie expenditure rate is placed in the counter 41 and transferred to the latch memory 60. Once this transfer has been effected, the counter 41 again may be used to enter new calorie input data into the system, as described previously, without disturbing the calorie expenditure rate which is stored in the latch memory 60.

Once the calorie expenditure rate is stored in the memory 60, the current rate at which calorie expenditure information is supplied from the rate controller 54 to the counter 36 may be read out by pushing the calorie rate pushbutton 23. This causes the "Enable 2" signal to be applied to the multiplexer gate and output driver circuit 38 to cause the output of the latch memory circuit to be displayed in the display 13. Depressing the rate key 23 at any time causes the display 13 to indicate the current calorie expenditure rate programmed into the calorie computer.

The output of the latch memory 60 is used in conjunction with a third digital down counter 62 to control the rate at which pulses are applied to the main counter 36 through the OR gate 51 in addition to those supplied by the basic basal rate circuit from the output of the counter 47. Once per second, the output of the latch memory 60 is jam fed to change the count of the counter 62 which then stores the new rate input. The counter 62 then is operated in a count "down" mode by a high speed clock on a lead 64 from the rate controller circuit 54 until it is emptied. A carryout pulse then is applied to the rate controller 54 from the counter 62 over a lead 65.

During the time interval from the time the information is first jam set into the counter 62 until the pulse is obtained on the carryout lead 65, pulses are applied through the OR gate 48, the divide circuit 50, and the OR gate 51 to decrement the main counter 36. The number of these pulses adjusts the calorie-per-hour information stored in the counter 62 to calories-per-second expended during the one second time interval between the successive resettings of the counter 62. Thus, the calorie expended rate set into the system by the operation of the pushbutton 20 continues to supplement the basal rate supplied through the OR gate 48 from the output of the counter 47 to control the net calorie expenditure which is continuously monitored by the counter 36.

In the event that the calories expended should equal the calorie input over the time interval being measured, the counter 36 is reset to its zero count and produces a carryout pulse on a lead 67. This pulse is applied to the rate controller 54 to terminate its operation. As soon as any new calorie input data is transferred to the main counter 36, the rate controller is free to operate to permit pulses to pass through it corresponding to the rate selected by the information which is updated each second in the calorie rate down counter 62. Alternatively, the circuit may continue to operate to count negative calories, i.e. the excess of calorie expenditure over calorie intake. In such an event, the carryout pulse from the counter 36 would not be applied to the gate 91 (which then would be eliminated), but instead could be used to indicate the negative count. This may be accomplished, for example, by pulsing the colon between the center two digits on the display. Once the calorie intake again exceeds the negative amount, such an indication would be removed. The technique used is conventional and of the type commonly used in hand-held electronic calculators.

For a better understanding of the operation of the controller circuit 40, reference now should be made to FIG. 3. The control circuit 40 comprises two toggle flip-flops 71 and 72 and two direct set/reset flip-flops 74 and 75 as its primary circuit components. Normally all four of these flip-flops are in their "reset" condition or state.

Assume now that the user of the system has just eaten an item of food representing a calorie intake of 80 calories. He wishes to enter this information into the calorie computer system. To do this, the Calorie In pushbutton 19 is depressed. This causes the toggle flip-flop 71 to change its state from its "reset" condition to its "set" condition. As a result, its "Q" output goes high and its "Q̄" output goes low. As soon as the flip-flop 71 is set, its Q output causes the flip-flop 74 to change from its "reset" state to its "set" state causing its Q output to go high. When the Q output of the flip-flop 74 goes high, it enables an AND gate 75 to pass the 2 Hertz clock pulses appearing on the lead 34 to the input of an INHIBIT gate 77.

At the time the flip-flop 71 switched to its "set" state, the INHIBIT gate 77 was enabled by the removal of an inhibiting input applied to it from the Q̄ output of the flip-flop 71. Thus, the clock pulses appearing on the lead 34 pass through an OR gate 78 to the lead 58 to advance the counter 41 one count for each pulse. As shown in FIG. 2, the counter 41 counts by tens; so that each time a pulse on the lead 34 is passed by the gates 75, 77 and 78, the cumulative total count in the counter 41 is increased by ten. This increase occurs once each one-half second. Thus, to add 80 calories to the system, the Calorie In key 19 is held depressed for 3½ seconds, at which time the display in the window 13 indicates 80. The pushbutton 19 then is released and depressed again to clear the display and enter the count 80 in the counter 41 into the main memory 36.

The second depression of the pushbutton 19 after its release toggles the flip-flop 71 to place it back in its "reset" state of operation. This causes the INHIBIT gate 77 to block the passage of any further pulses from the output of the gate 75. At the same time, both of the upper two inputs to an AND gate 80 are now high or enabling inputs; so that the high speed clock pulses appearing on the lead 33 are now passed by the gate 80. These pulses are applied directly over the lead 43 to the OR gate 51 and the rate controller 54. As described previously, the rate controller causes the counter 36 to be placed in its "up" count direction and the pulses then passed by the OR gate 51 advance the count in the counter 36 one count (one calorie) for each pulse.

Since the counter 36 counts units and the counter 41 has a minimum count of 10, a divide-by-10 circuit 81 is connected to the output of the AND gate 40 to supply pulses to the OR gate 78. These pulses, as described previously, appear on the lead 58 to operate the counter 41. The direction of count of the counter 41 is controlled by the signal on the lead 44 which in turn is produced by signals applied to an OR gate 83. The counter 44 counts in its up direction whenever the toggle flip-flop 41 is in its "set" state, with the Q output high. Thus, the counter adds to its count during the time that the 2 Hertz clock pulses on the lead 34 are operating the counter to add calorie information to it.

When the toggle flip-flop 71, however, is in its reset condition, as is now the case, the up-down control signal on the lead 44 changes to cause the counter 41 to count in its down or reverse direction. Thus, the previously entered calorie input information is removed from the counter 41 under the control of the clock pulses passed by the gate 80.

When the counter 41 reaches its zero count, a carryout pulse is applied from the counter over the lead 45. This pulse is passed through an OR gate 85 to the reset inputs of the toggle flip-flops 71 and 72 to set these flip-flops to their reset state if this already has not been accomplished. In addition, the carryout pulse is applied to a second OR gate 86, the output of which is connected to the reset input of flip-flop 74 to reset the flip-flop 74 to its "reset" state. When this occurs, the AND gate 80 no longer is enabled since the Q output of the flip-flop 74 goes low. Thus, no more pulses are applied over the lead 43 to the rate controller 54 and the OR gate 51. The number of pulses required to do this is precisely equal to the count which was entered originally into the counter 41. Thus, the calorie input information has been transferred to the main calorie counter 36.

The operation of the control circuitry to establish the calorie expenditure rate also may be understood by reference to FIG. 3. When an entry is to be made into the counter 41 indicative of a calorie expenditure rate, the pushbutton 20 is depressed as described previously. This causes the state of the toggle flip-flop 72 to change from its "reset" state to its "set" state. Thus, the Q output of the flip-flop 72 goes high to cause the up/- down control on the lead 44 to the counter 41 to operate the counter 41 in its "up" direction. At the same time, a "preset enable" signal is applied over the lead 57 to the counter 41 to force the counter to increase its count by 50 instead of 10 for the application of each clock pulse to the counter, so long as the signal is present on the present enable lead 57.

When the flip-flop 72 is set to its "set" state, the high Q output also causes the direct set flip-flop 75 to be set from its "reset" to its "set" state of operation. This causes the Q output of the flip-flop 75 to go high, enabling an AND gate 88 to pass the 1 Hertz clock pulses on the lead 35 through the OR gate 78 to the clock input 58 of the counter. Thus, each time a 1 Hertz pulse is applied over the lead 58 to the counter, the count in the counter increases by 50. So long as the pushbutton 20 is depressed, the display in the display window 13 indicates the output condition of the counter to show the calorie rate expenditure being entered into the counter 41.

When the desired rate is reached, the pushbutton 20 is released and then depressed again. This causes the toggle flip-flop 72 to change its state from its "set" state to its "reset" state, at which time the present enable signal on the lead 57 is removed. At the same time, the flip-flop 75, which is coupled directly to the outputs of the flip-flop 72, is set to its "reset" condition, causing the AND gate 88 to be disabled. When the $\overline{Q}$ output of the flip-flop 72 first goes high, it produces a signal to the latch memory circuit 60 to cause it to store the information present on the outputs of the counter 41. This is the condition described previously which permits the data in the latch memory 60 to be continuously jam fed or set into the counter 62 under operation of the rate controller circuit 54.

To insure that the system is cleared prior to the entry of any calorie input data or calorie expenditure data, a reset pushbutton 26 is provided. This pushbutton provides signals to the OR gates 85 and 86 to result in a resetting of all of the flip-flops 71 to 75 to their "reset" state of operation. It may not be necessary to operate the reset pushbutton, but its operation insures that the circuit is in its proper state of operation prior to the entry of any new data under the control of the pushbutton 19 or 20.

Reference now should be made to FIG. 4 which is a detailed circuit diagram of the rate controller circuit 54. As stated previously, the rate controller circuit 54 controls the direction of the count of the counter 36 through a signal applied over the lead 53. Normally the lead 53 produces an output which causes the counter 36 to count in its down direction. However, whenever input pulses continuously appear on the lead 43, representative of the transfer of calorie input information to the counter 36, the signal on the lead 53 causes the counter 36 to count in its up direction. This is controlled or accomplished by applying the pulses on the lead 43 to a retriggerable one-shot multivibrator circuit or missing pulse detector circuit 90 which is held in its astable output state so long as the high frequency pulses appear on the lead 43. The time-out period for the circuit 90 is selected to be only slightly longer than the time interval between successive pulses at the high frequency rate on the lead 43. As described previously, unless data is being transferred from the counter 41 to the main counter 36, no pulses whatsoever appear on the lead 43; so that the retriggerable one-shot multivibrator circuit 90 normally remains in its stable state.

So long as some count is stored in the counter 36, the signal on the carryout lead 67 is a low signal which enables an INHIBIT gate 91 to pass the 1 Hertz clock pulses appearing on the lead 35 to the set input of a direct set flip-flop 94. Assume initially that the flip-flop 94 is in its "reset" state of operation. In this state, the Q output of the flip-flop is low and the $\overline{Q}$ output is high; so that an AND gate 96, which has the high frequency clock pulses on the lead 33 applied to its other input, is normally disabled.

The next 1 Hertz clock pulse appearing on the lead 35 then passes through the enabled INHIBIT gate 91 to set the flip-flop 94 from its "reset" to its "set" condition of operation. When this occurs, the Q output of the flip-flop goes high and the $\overline{Q}$ output goes low; so that the AND gate 96 is opened to pass pulses from the lead 33 to the OR gate 48, described previously in conjunction with FIG. 2.

These pulses also are applied to a divide-by-10 circuit 98 and appear as the clock pulses on the lead 64 used to operate the count down counter 62. The reason the divider 98 is used is that the minimum count or lowest increment of count in the counter 62 is 10 whereas the count in counter 36 is 1. Thus, the divider 98 is necessary to maintain the proper ratio between the pulses appearing at the output of the OR gate 48 and those appearing on the lead 64.

As described previously, the rate which is stored in the counter 62 is an hourly rate, so that the divide-by-3600 divider 50 is interposed between the output of the gate 48 and the input to the counter 36. The number of pulses required to drive the counter 62 to its zero count then is directly proportional to a calorie per second consumption rate represented by the pulses applied to the counter 36 from the OR gate 51. As soon as the counter 62 is cleared, a carryout pulse is produced on the lead 65 to reset the flip-flop 94 to its original condition. This removes the enabling input for the AND gate 96, and no further pulses are passed by that gate.

At this time, however, the $\overline{Q}$ output of the flip-flop 94 goes high to apply a pulse over the set enable lead 99 to the counter 62 to cause the counter 62 again to be jam set with the count stored at that time in the latch memory 60. This readies the circuit for the next operation. Subsequently, when the next pulse appears on the lead 35, the sequence of operation is repeated. The number of pulses which are passed by the AND gate 96 during each one second interval varies in accordance with the count which is stored in the counter 62. Thus, over an average period of time, the change in the count decrement of the counter 36 varies at a rate which is in accordance with the calories per hour expenditure rate stored in the latch memory 60.

The reset pushbutton switch 26 may be used to selectively reset certain ones of the circuits as described previously. Or in addition this switch may be used as a master reset switch to reset all of the counters and all of the circuits to an initial state of operation, thus acting as a complete system "clear" reset button. The particular application of this reset function may be varied to accommodate different design considerations.

The foregoing description describes technically what occurs in the operation of the calorie computer-chronometer circuit used in conjunction with a conventional electronic digital wristwatch. As described previously, the device is first calibrated to subtract the proper basal fraction expenditure of the user. Ideally this setting of the switch 49 is done after determination of the exact rate by a physician competent in metabolic processes, but such an adjustment may be made by an individual with relatively good accuracy.

In the use of this system, a typical sequence may be as follows. Each time food is consumed (food being defined as any digestible material containing energy), the caloric content is entered as described previously by depression of the Calorie In pushbutton 19. For example, assume that the user at 8 A.M. has a breakfast of two slices of bacon (100 calories), two fried egg (220 calories), one slice of buttered toast (160 calories), and two cups of black coffee (2 calories). The total, rounded out to the nearest tens (480), is entered. Similar entries may be made for a coffee break, a snack or lunch; and each time the entries are made in accordance with the procedure mentioned above.

As previously noted, the energy required for basic bodily metabolic action is automatically and continuously subtracted. Different activities however result in the expenditures of additional amounts of energy. Assume that the user of the unit in the morning activates the Calorie Expenditure pushbutton 20 to set into the system the appropriate rating for bathing, his ensuing activity (100 calories expended per hour). The appropriate entries into the system automatically effect this additional activity to be considered in the main calorie counter 36. After 20 minutes, the user emerges and resets his calorie expenditure input to 50 to cover his activity level for dressing. This level also is correct for eating and driving to his office. Upon arriving at his office building, the user decides to walk to his fourth floor office. He enters 800 (the expenditure per hour for climbing stairs). When he arrives at his office he re-enters 50 which is the appropriate hourly calorie expenditure for the office work he will be doing. Different entries of various type are made as the calorie rate expenditure occurs throughout the day.

It is not necessary for the user to keep track of the total elapsed time at which he is engaged in different calorie expenditure rate activities, since the clock circuit provided by oscillator 31 in the time computer circuit portion of the watch automatically takes care of this for him in conjunction with the other circuitry, the operation of which has been described above. At any time, the user may verify his calorie expenditure rate by depressing the calorie rate button 23. Also, whenever he desires he can determine the net calories unexpended which he has remaining in the counter 36 by depressing the pushbutton 22. Since the system is incorporated into a wristwatch, it is in a form which will be with the user wherever he goes and he can conveniently and quickly make the necessary entries to maintain the calorie data.

We claim:

1. In an electronic timepiece having a source of constant frequency signals pulses, a time computing circuit coupled to the source of constant frequency signal pulses and producing time information in binary coded decimal form, an electro-optical digital display, a decoder circuit coupling the time computer circuit to the display, and a first manually operated switch coupled to the time computing circuit for energizing the display from the time computing circuit in response to operation of such first switch, an auxiliary calorie calculator data system including in combination:

a main storage counter for storing numerical data indicative of net calories;

a rate controlling circuit coupling said main counter with said source of constant frequency pulses for decrementing the count in said main counter at a predetermined rate;

an auxiliary digital counter;

means including at least a second manually operated switch coupled with said auxiliary counter and with said source of constant frequency pulses to store a count in said auxiliary counter corresponding to caloric intake, said second switch further being coupled with said auxiliary counter for energizing said display from the output of said auxiliary counter in response to operation of said second switch;

means controlled by said second switch for transferring the count from said auxiliary counter to said main counter to increase the count in said main counter by the amount of the count stored in said auxiliary counter;

calorie rate expenditure circuit means including a third manually operated switch for effecting storage of a count in said auxiliary counter corresponding to the rate of expenditure of calories;

a latch memory circuit coupled with said auxiliary counter and operated by said third switch for storing the count present in said auxiliary counter;

a calorie rate down-counter coupled with said latch memory circuit and with said rate controlling circuit for temporarily storing the calorie count stored in said latch memory circuit and for varying the rate at which the count in the main counter is decremented by said rate controlling circuit directly proportional to the count stored in said latch memory circuit; and a fourth manually operated switch coupled with said main counter for energizing said display from said main counter in response to operation of said fourth switch.

2. In an electronic timepiece including a source of constant frequency signals, a time computing circuit coupled to the source of constant frequency signals and an electro-optical digital display where the time computing circuit produces time information in binary coded form to a decoder coupling the time computer circuit to said display, and means coupled with the time computing circuit for energizing said display in response to operation of such means, an auxiliary data system including in combination:

main auxiliary storage counter circuit means for storing numerical data other than time and date data;

means including at least first manually operated switch coupled with said main auxiliary storage counter circuit means for effecting the storage of data therein; means coupled with said source of constant frequency signals and with said main auxiliary storage counter circuit means for applying pulses from said source of constant frequency signals to said counter circuit means for decrementing the count in said counter circuit means upon the application of each of said pulses thereto;

further means coupled with said counter circuit means for selectively supplying additional pulses to said counter circuit means over predetermined time intervals to further decrement the count in said counter circuit means in response to each of such additional pulses; and means including a second manually operated switch coupling the output of said counter circuit means with the decoder for energizing the display from said counter circuit means in response to operation of said second switch.

3. The combination according to claim 2, wherein said counter circuit means is a main counter and further including at least one auxiliary counter and a third manually operated switch for coupling said auxiliary counter with the source of constant frequency signals for entering a numerical count in said auxiliary counter corresponding to caloric input, and means coupling the output of said auxiliary counter with the decoder for energizing the display from said auxiliary counter in response to operation of said third manually operated switch, and means for transferring the count in said auxiliary counter to said main counter to increase the count in said main counter by the amount of the count entered into said auxiliary counter.

4. The combination according to claim 3, further including a calorie rate down-counter, a latch memory and a fourth manually operated switch, wherein said fourth manually operated switch is coupled with said auxiliary counter and said source of constant frequency signals to cause said auxiliary counter to store a count therein indicative of a calorie expenditure rate, said latch memory being coupled with said auxiliary counter and with said fourth switch to store the count in said auxiliary counter in response to operation of said fourth switch; said calorie rate down-counter being coupled with said latch memory for receiving and storing the data in said latch memory in response to predetermined pulses from said source of constant frequency signals; and means coupling said calorie rate down-counter with said means for changing the data in said main counter for controlling data stored in said main counter.

* * * * *